US 9,757,515 B1

(12) United States Patent
Patel

(10) Patent No.: US 9,757,515 B1
(45) Date of Patent: Sep. 12, 2017

(54) MULTI-LOCATION TOP LOADING INSULIN INFUSION SET

(71) Applicant: Flextronics AP, LLC, Broomfield, CO (US)

(72) Inventor: Lopa Rishi Patel, Irving, TX (US)

(73) Assignee: Flextronics AP, LLC, Broomfield, CO (US)

( * ) Notice: Subject to any disclaimer, the term of this patent is extended or adjusted under 35 U.S.C. 154(b) by 462 days.

(21) Appl. No.: 14/515,430

(22) Filed: Oct. 15, 2014

Related U.S. Application Data

(60) Provisional application No. 61/891,845, filed on Oct. 16, 2013.

(51) Int. Cl.
*A61M 5/162* (2006.01)

(52) U.S. Cl.
CPC .................... *A61M 5/162* (2013.01)

(58) Field of Classification Search
CPC ........... A61B 17/34; A61B 2017/3419; A61B 17/3494; A61M 25/0606; A61M 25/0102; A61M 2039/229; A61M 39/223
USPC ...................... 604/244, 174, 164.01–164.05; 128/DIG. 26
See application file for complete search history.

(56) References Cited

U.S. PATENT DOCUMENTS

| | | | |
|---|---|---|---|
| 4,755,173 A * | 7/1988 | Konopka | A61M 25/0606 128/DIG. 26 |
| 5,976,165 A | 11/1999 | Ball et al. | |
| 6,685,674 B2 * | 2/2004 | Douglas | A61M 5/158 604/167.05 |
| 6,736,797 B1 * | 5/2004 | Larsen | A61M 5/158 604/167.05 |
| 8,398,586 B2 * | 3/2013 | Lynch | A61M 5/158 604/164.01 |
| 2005/0010134 A1 | 1/2005 | Douglas | |
| 2006/0217636 A1 | 9/2006 | Braig | |
| 2008/0103450 A1 * | 5/2008 | Marrs | A61M 5/158 604/174 |
| 2008/0146966 A1 | 6/2008 | Levaughn et al. | |
| 2010/0174237 A1 | 7/2010 | Halaka | |
| 2012/0065487 A1 | 3/2012 | O'Malley | |
| 2012/0302939 A1 | 11/2012 | Bral | |
| 2012/0302956 A1 | 11/2012 | Bral | |
| 2014/0142507 A1 | 5/2014 | Armes | |

* cited by examiner

*Primary Examiner* — Manuel Mendez
(74) *Attorney, Agent, or Firm* — Haverstock & Owens LLP

(57) ABSTRACT

A manual infusion set comprises a top connector lockable in a plurality of positions. The top connector and tubing is initially loaded from the top and then slid forward in order to puncture the septum. Once the connector is attached, it cannot be rotated. With the connector locked in place, flexible tubing connects the septum hub with a medicine pump, which continually supplies medicine such as insulin to a user.

23 Claims, 6 Drawing Sheets

SECTION A-A

SECTION B-B

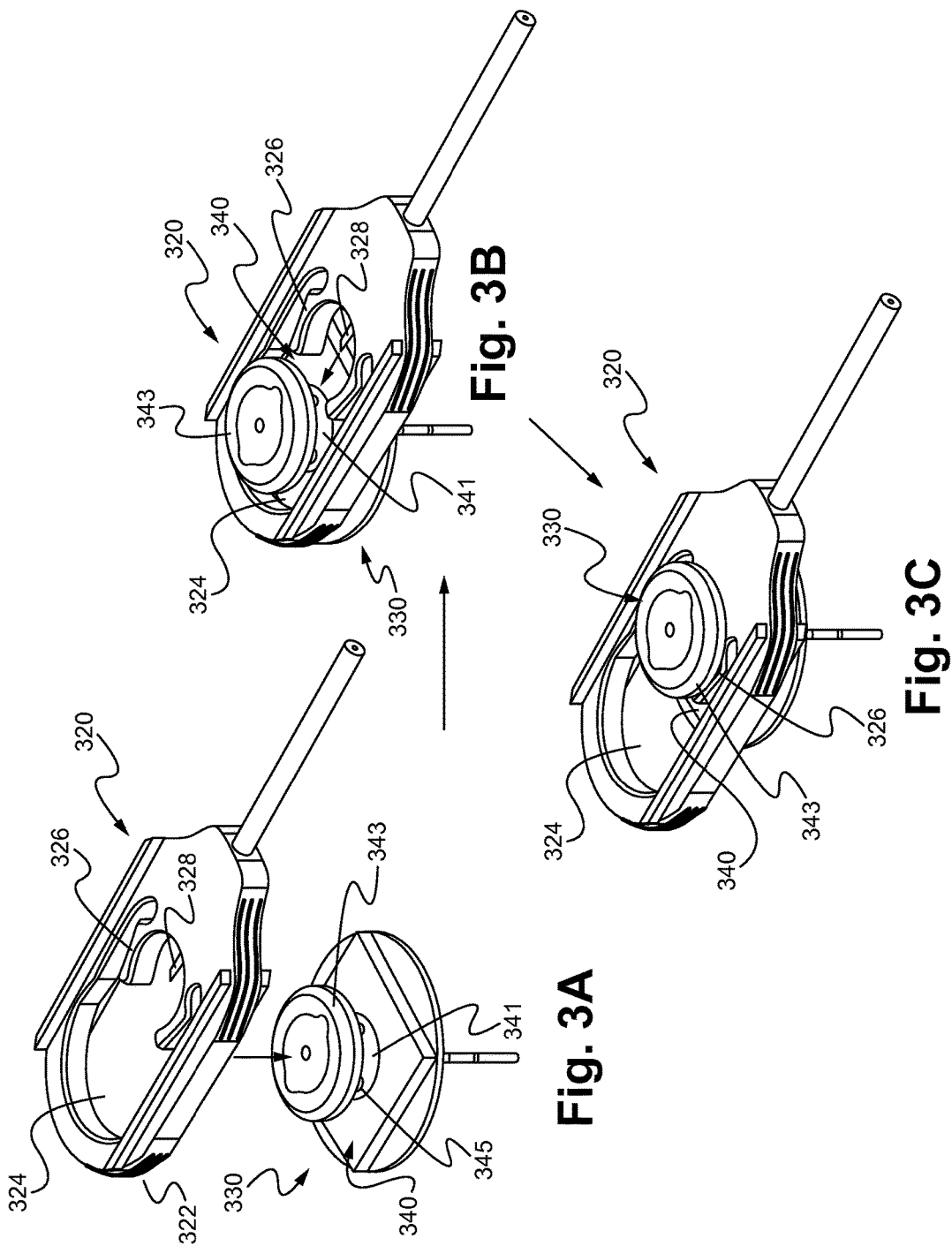

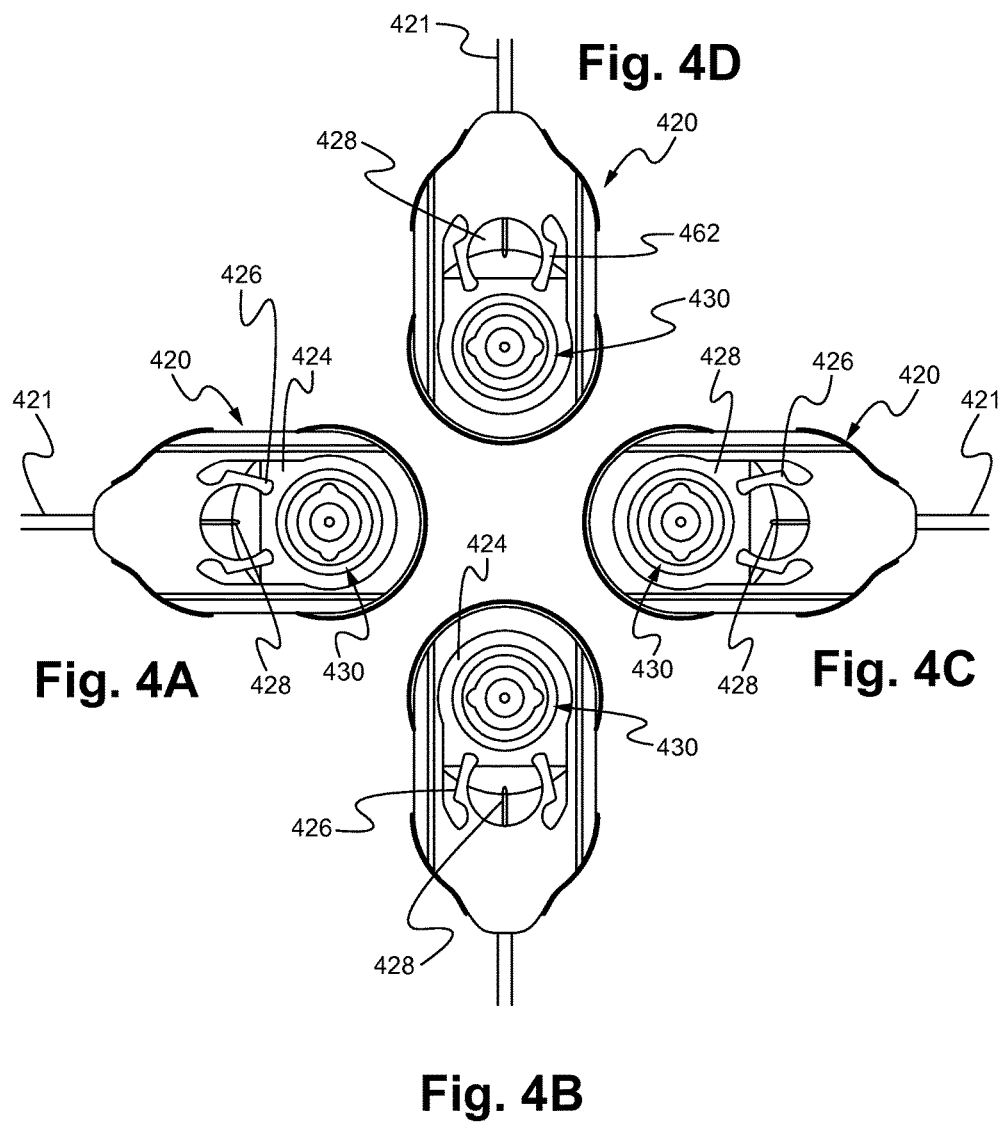

MULTI-LOCATION TOP LOADING INSULIN INFUSION SET

RELATED APPLICATIONS

This Patent application claims priority under 35 U.S.C. 119(e) of the U.S. provisional patent application, Application No. 61/891,845, filed on Oct. 16, 2013, and entitled "MEDICAL DEVICE-LCIS," which is also hereby incorporated by reference in its entirety.

FIELD OF THE INVENTION

The present invention is generally directed to medical devices and drug delivery systems. More particularly, the present invention is directed to an infusion set for a subcutaneous delivery of a medication.

BACKGROUND OF THE INVENTION

An infusion set is used to connect a medicine delivery device to the body, similar to an intravenous line. A needle housed in a plastic tube or soft cannula is used to puncture the skin in order to insert the soft cannula under the skin where the medicine can be delivered. After insertion, the needle is removed and the soft cannula remains in place. Often, a site anchors the soft cannula to the area with an adhesive or tape. Flexible tubing connects the site to a pump, which supplies medicine to the area. Prohibitively, many infusion sets require an automated insertion device and are not cost effective. Further, it can be necessary to change the orientation of the infusion set in order to move the flexible tubing so that it does not become crimped or impeded and a steady supply of medicine is continuously received or delivered as required.

SUMMARY OF THE INVENTION

A manual infusion set comprises a top connector lockable in a plurality of positions. The top connector and tubing is initially loaded from the top and then slid forward so that a septum pierce punctures the septum. Once the connector is attached, it cannot be rotated. With the connector locked in place, flexible tubing connects the septum hub with a medicine pump, which continually or intermittently supplies medicine such as insulin to a user.

In one aspect, an infusion set comprises a top connector comprising an aperture and a septum pierce and a septum hub, wherein the top connector is placed over the septum hub slid forward in order to couple with the septum hub and lock into place. The septum hub comprises a septum within an interior of the hub. In some embodiments, the septum pierce pierces a side of the septum when the top connector is locked into place. The top connector is lockable in a plurality of positions. For example, in some embodiments, the top connector is lockable in a plurality of positions around a circumference of the septum hub. The top connector is non-rotatable once it is locked into place. In some embodiments, the top connector comprises a u-shaped locking ring for coupling with the septum hub. The infusion set further comprises an introducer needle for introducing a soft cannula to a subcutaneous layer of skin. In some embodiments, the infusion set is configured to couple to an insulin pump.

In another aspect, a method of coupling a medicine pump with a septum hub of an infusion site comprises placing a top connector over and around the septum hub and sliding the top connector forward in order to pierce a septum of the septum hub and lock the top connector into place. In some embodiments, the top connector pierces a side of the septum when the top connector is locked into place. The top connector is lockable in a plurality of positions. For example, in some embodiments, the top connector is lockable in a plurality of positions around a circumference of the septum hub. The top connector is non-rotatable when it is locked into place. In some embodiments, the top connector comprises a u-shaped locking ring for coupling with the septum hub. In some embodiments, the medicine pump is configured to deliver insulin to the site. In some embodiments, the method comprises disconnecting the top connector. After the top connector is disconnected, it cab be reconnected. In some embodiments, when the top connector is reconnected, it is reconnected in a different position.

In a further aspect, a one-piece top connector configured for coupling with a medicine pump and a septum hub of an infusion set comprises a one-piece body comprising an aperture that passes through the one-piece body and a septum pierce. Particularly, the aperture is configured to fit around the septum hub. In some embodiments, the top connector comprises a u-shaped locking ring for coupling with the septum hub. The top connector is lockable in a plurality of positions around a circumference to the septum hub.

BRIEF DESCRIPTION OF THE DRAWINGS

Several example embodiments are described with reference to the drawings, wherein like components are provided with like reference numerals. The example embodiments are intended to illustrate, but not to limit, the invention. The drawings include the following figures:

FIGS. 3A-3C illustrate an infusion set in accordance with some embodiments.

FIGS. 4A-4D illustrate an infusion set in accordance with some embodiments.

DETAILED DESCRIPTION OF THE EMBODIMENTS

Embodiments of the invention are directed to a manual infusion set in which the top connector is lockable in a plurality of positions. The top connector and tubing is initially loaded from the top and then slid forward in order to puncture the septum. Once the connector is attached, it cannot be rotated.

Reference will now be made in detail to implementations of a multi-location top loading infusion set. The same reference indicators will be used throughout the drawings and the following detailed description to refer to the same or like parts. In the interest of clarity, not all of the routine features of the implementations described herein are shown and described. It will be appreciated that in the development of any such actual implementation, numerous implementation-specific decisions can be made in order to achieve the developer's specific goals, such as compliance with application and business related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Figure 1:
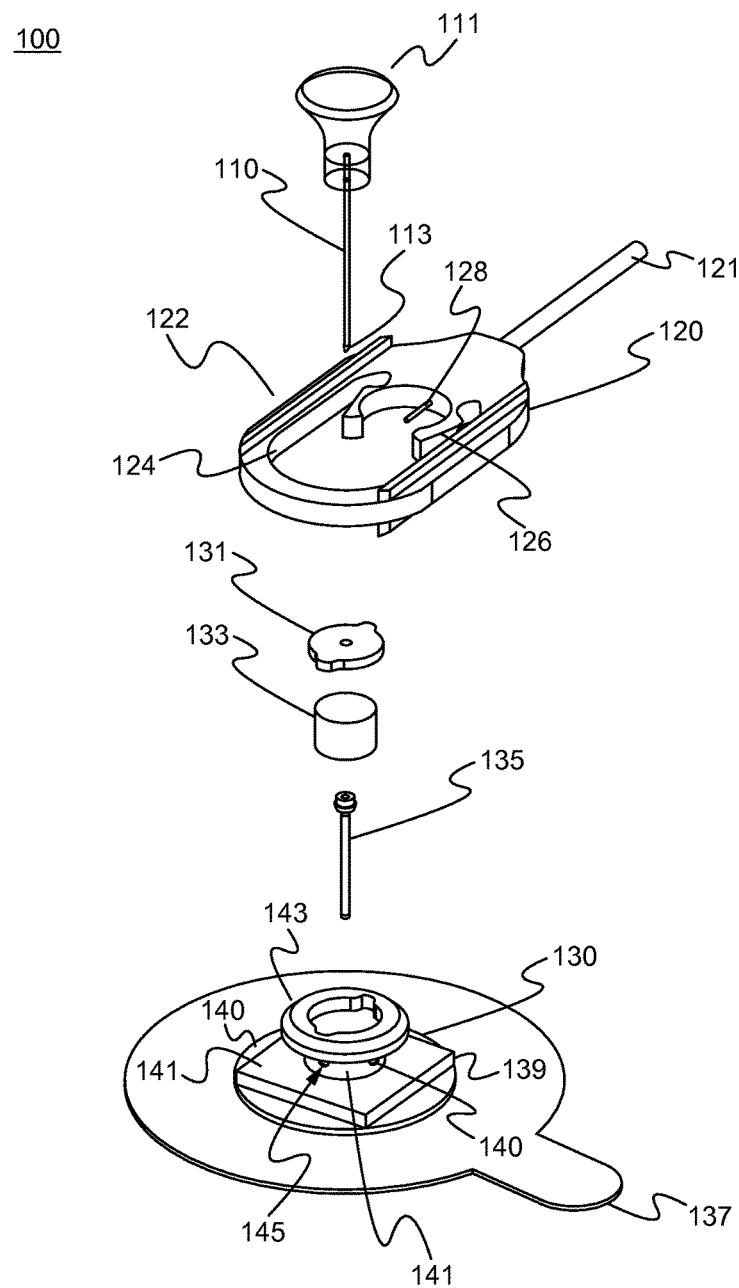
FIG. 1 illustrates an exploded view of an infusion set in accordance with some embodiments.

Referring now to FIG. 1, an exploded view of an infusion set is depicted therein. The infusion set 100 comprises a connector 120 and a septum hub 130. The septum hub 130 comprises an adhesive layer 137, a base 139, a soft cannula 135, a septum 133 and a cap 131. As shown within FIG. 1, the septum hub 130 also comprises an inner cylinder 140 with an upper ring 143 and a puncture area 141 comprising one or more puncture points 145. The septum 133 fits within the inner cylinder 140 and the cap 131 fits on top of the septum 133 and the inner cylinder 140. The soft cannula 135 contacts an inside of the septum 133 within the inner cylinder 140 and extends from a bottom of the septum hub 130.

The connector 120 comprises a single part, one-piece body 122. The connector 120 comprises a soft tube 121, an aperture 124, a septum pierce 128, and a locking ring 126 which wraps around the septum pierce 128.

As further shown in FIG. 1, an introducer needle 110 comprises a handle 111 and a needle point 113. In some embodiments, the introducer needle 110 is spring loaded with an auto insertion device.

Figure 2A:
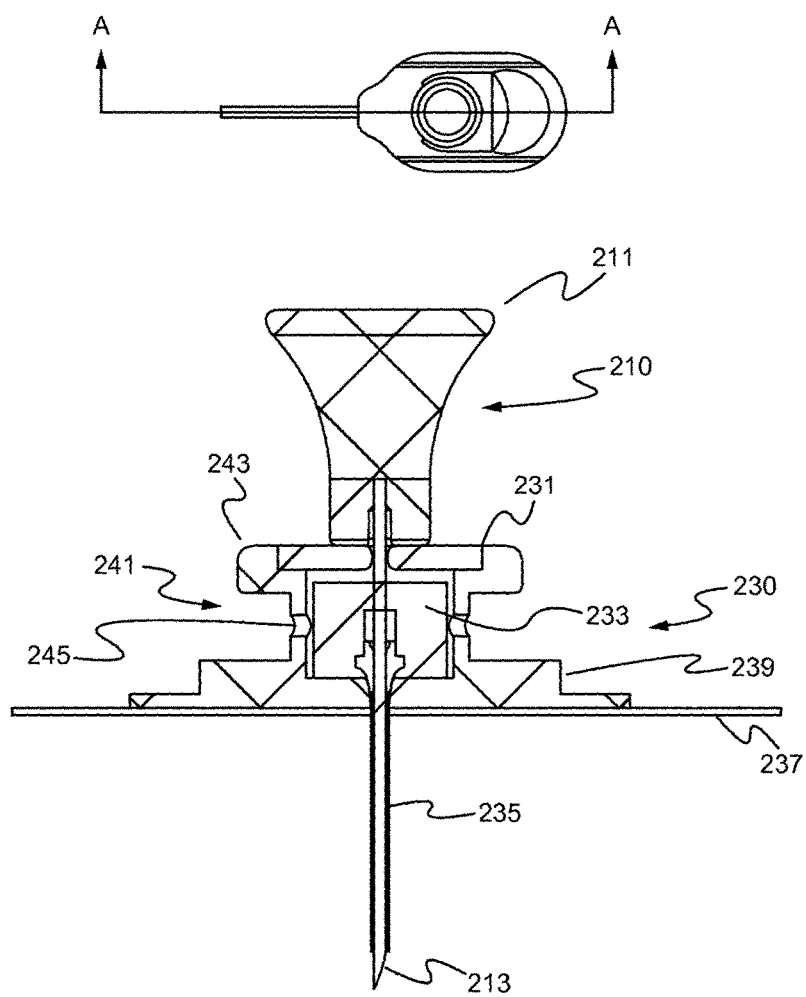
FIGS. 2A and 2B illustrate a sectional view of an infusion set and insertion needle in accordance with some embodiments.

FIG. 2A illustrates a sectional view of the septum hub 230 in an assembled configuration, in accordance with some embodiments. The septum hub 230 is similar to the septum hub 130, as described above. The septum hub 230 comprises an comprises an adhesive layer 237, a base 239, a soft cannula 235, a septum 233 and a cap 231. As shown within FIG. 2A, the introducer needle 210 has been inserted into the septum hub 230 and through the soft cannula 235. As described above, in some embodiments, the introducer needle 210 is spring loaded. The soft cannula 235 is introduced into a subcutaneous cutaneous layer of the ski using introducer needle 210. After the soft cannula 235 is introduced to the skin, the introducer needle 210 is removed and the soft cannula 235 remains in place. The septum hub 230 anchors the soft cannula 235 in place by pressing the adhesive layer 237 against a user's skin. The flexible tubing 221 connects the septum hub 230 with a medicine pump (not shown), which continually supplies medicine to a user.

Figure 2B:
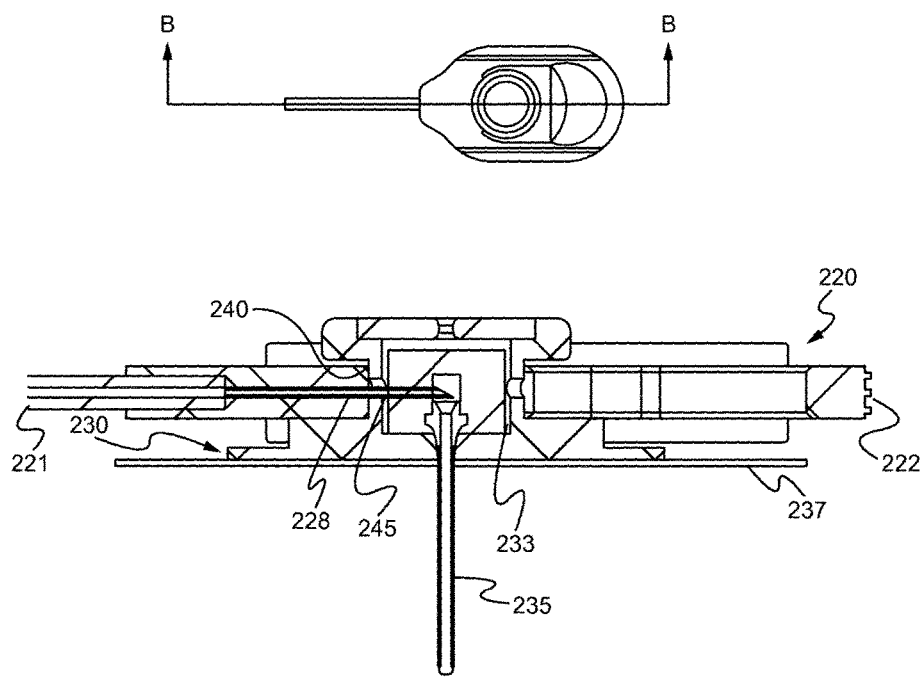

FIG. 2B illustrates a sectional view showing the connector 220 removably coupled with the septum hub 230. The connector 220 is initially loaded from the top and then slid forward so that the septum pierce 228 punctures the septum 233. The connector 220 comprises a single part, one-piece body 222. As shown within FIG. 2B, the septum pierce 228 has punctured the septum 233 at the puncture area 241 of the septum hub 230 within the inner cylinder 240. The septum pierce 228 connects the flexible tubing 221 with the septum 233 and the soft cannula 235, in order to supply medicine to the subcutaneous layer of the skin through the soft cannula 235. In some embodiments, a plurality of puncture points 245 surround the inner cylinder 240 and the septum 233. Consequently, the connector 220 can be connected at different orientations and in a plurality of positions around the circumference of the inner cylinder 240. For example, in some embodiments, the connector 220 connects to four different points around the circumference of the inner cylinder 240. In some embodiments, the connector 220 is locked in place when it is coupled with the septum hub 230. Additionally, as shown within FIG. 2B, when the connector is locked in place, the septum pierce 238 pierces a side of the septum 233.

As described above, the connector is initially loaded from the top and then slid forward in order to connect with the septum hub. FIGS. 3A-3C illustrate an infusion set in accordance with some embodiments. As shown in FIG. 3A, in order to couple the connector 320 with the septum hub 330, the connector is placed over a top of the septum hub 330. As shown in FIG. 3B, the aperture 324 of the connector body 322 is placed over and around the inner cylinder 340 and with the cylinder 340 at a back and opposite end of the aperture from the locking ring 326 and the septum pierce 328. The connector 320 is then pushed forward so that the septum pierce 328 punctures the septum and the connector 320 removably couples with the septum hub 330. Once coupled with the septum hub 330, the connector 320 locked in place so that it is not laterally movable. To remove the connector 320 from the septum hub 330, the connector 320 is pulled backward from the septum hub 330 and over the inner cylinder 340. As described above, in some embodiments, the connector 320 is lockable in a plurality of positions around the septum hub 330. For example, in some embodiments, the connector 320 is separately lockable in four locations around the septum hub 330.

As further shown within FIGS. 3B and 3C, when the connector 320 couples with the septum hub 330, the locking ring 326 surround the inner cylinder 340 under the upper ring 343 and around the puncture area 341. In some embodiments, the locking ring 326 snap and/or friction fits around the inner cylinder 340 in order to lock the connector 320 in place. Alternatively, in some embodiments, the connector 320 is locked into place by the interaction of the septum pierce 328 and the inner ring.

As described above, in some embodiments, the top connector is lockable in a plurality of positions around the circumference of the septum hub. FIGS. 4A-4D illustrate a top connector 420 removably coupling with a septum hub 430 and around a plurality of positions around a circumference of the septum hub 430. For example, in some embodiments, the connector 420 removably couples in four positions around the septum hub 430 spaced approximately 90° apart from each other around the septum hub 430. However, the connector 420 is able to couple with any appropriately desired positions around the septum hub 430. As described above, in order to couple with the septum hub 430, the aperture 424 is placed over and around the septum hub 430 is slid forward so that the septum pierce 428 pierces the septum and the connector is locked in place. In some embodiments, the locking ring 426 surrounds a side of the septum hub 430 and the connector 420 is locked in place. With the connector 420 locked in place, flexible tubing 421 connects the septum hub 430 with a medicine pump (not shown), which continually supplies medicine to the user.

Figure 5:
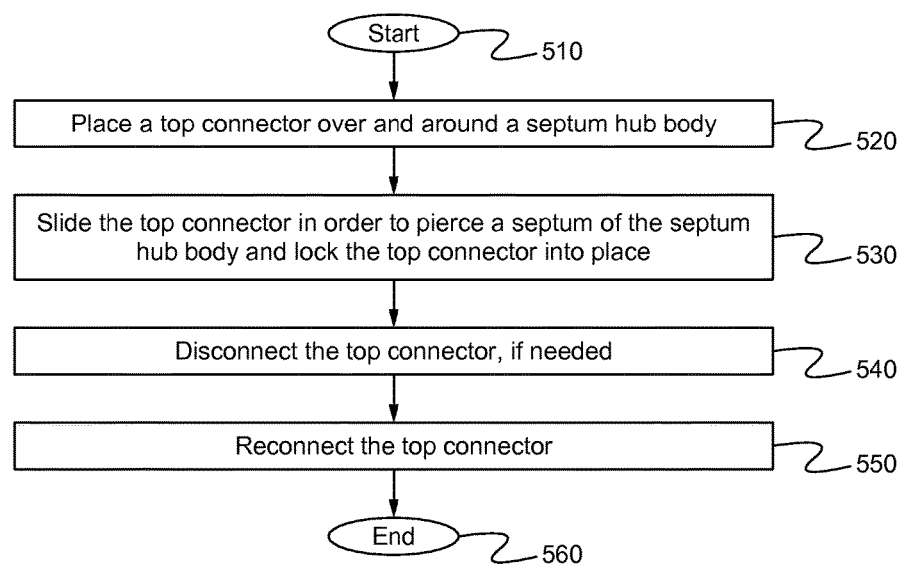
FIG. 5 illustrates a method of coupling a tubing set with an infusion site in accordance with some embodiments.

FIG. 5 illustrates a method of coupling a medicine pump in accordance with some embodiments. The method begins in the step 510. In the step 520, a connector for connecting a septum hub is placed over and around a septum hub body. In some embodiments, the top connector is a single-piece top connector. Then, in the step 530, the top connector is slid into place in order to couple with the septum hub. The top connector is lockable in place when it is coupled into place. In some embodiments, the connector pierces a side of a septum of the septum hub when it is coupled with the septum hub. The connector is lockable in a plurality of positions around a circumference of the septum hub. In some embodiments, the connector comprises a locking ring which snap-fits with the septum hub. As described above, with the connector locked in place, flexible tubing connects the septum hub with a medicine pump, which continually supplies medicine to the user.

In operation, a single piece connector couples to a septum hub in order to complete an infusion set and deliver medicine to a subcutaneous area of the body. The connector is coupled to the septum hub by loading the connector over a top of the septum hub and sliding the connector forward so that a side of the septum is pierced. The connector couples to the septum hub in a plurality of positions and is lockable in place so that it cannot be rotated. Particularly, a user can easily slide the connector over the septum in order to securely lock the connector to a septum hub in order to quickly and efficiently couple the connector with the septum hub. Additionally, because the connector is lockable in a plurality of orientations, the connector can be placed in a position where the tubing is out of way of the user and can maintain a steady supply of medicine. In this manner, the medicine pump can continually supply medicine to a user. Accordingly, the multi-location top loading insulin infusion set as described herein has many advantages.

The present invention has been described in terms of specific embodiments incorporating details to facilitate the understanding of the principles of construction and operation of the invention. Such references, herein, to specific embodiments and details thereof are not intended to limit the scope of the claims appended hereto. It will be apparent to those skilled in the art that modifications can be made in the embodiments chosen for illustration without departing from the spirit and scope of the invention. Specifically it will be apparent to someone of ordinary skill in the art that the invention is able to be used with an appropriate intravenous medication.

What is claimed is:

1. An infusion set comprising:
   a. a top connector comprising:
      i. an aperture; and
      ii. a septum pierce; and
   b. a septum hub,
   wherein the top connector is placed over the septum hub and slid forward such that septum hub is moved from a first location in the aperture of the top connector to a second location in the aperture of the top connector in order to couple therewith and lock into place.

2. The infusion set of claim 1, wherein the septum hub comprises a septum within an interior of the hub, and a cap positioned over the septum and fits within an upper ring of the septum hub such that a top surface of the cap is flush with a top surface of upper ring of the septum hub.

3. The infusion set of claim 2, wherein the septum pierce pierces a side of the septum when the top connector is at the second location in the aperture of the top connector and is locked into place.

4. The infusion set of claim 1, wherein the top connector is lockable in a plurality of positions.

5. The infusion set of claim 4, wherein the top connector is lockable in a plurality of positions around a circumference to the septum hub.

6. The infusion set of claim 1, wherein the top connector is non-rotatable when it is locked into place.

7. The infusion set of claim 1, wherein the top connector comprises a u-shaped locking ring for coupling with the septum hub when the septum hub is at the second location in the aperture of the top connector, wherein legs of the u-shaped locking ring extend towards the first location of the aperture in the top connector.

8. The infusion set of claim 1, further comprising an introducer needle.

9. The infusion set of claim 1, wherein the infusion set is configured to couple to an insulin pump.

10. A method of coupling a medicine pump with a septum hub of an infusion site comprising:
    a. placing a top connector over and around the septum hub; and
    b. sliding the top connector forward in order to pierce a septum of the septum hub and lock the top connector into place.

11. The method of claim 10, wherein the top connector pierces a side of the septum when the top connector is locked into place.

12. The method of claim 10, wherein the top connector is lockable in a plurality of positions.

13. The method of claim 10, wherein the top connector is lockable in a plurality of positions around a circumference to the septum hub.

14. The method of claim 10, wherein the top connector is non-rotatable when it is locked into place.

15. The method of claim 10, wherein the top connector comprises an aperture formed therethrough, and a u-shaped locking ring located at one end of the aperture and including legs extending towards another end of the aperture and for coupling with the septum hub when the top connector is slid forward.

16. The method of claim 10, wherein the medicine pump is configured to deliver insulin to the site.

17. The method of claim 10, comprising disconnecting the top connector.

18. The method of claim 17, comprising reconnecting the top connector.

19. The method of claim 18, wherein the top connector is reconnected in a different position.

20. The top connector of claim 17, wherein the one-piece body further comprises a u-shaped locking ring that is located at a second end of the aperture and that includes legs extending towards a first end of the aperture and for coupling with the septum hub.

21. The top connector of claim 20, wherein the aperture is sized to accept the septum hub at the first end of the aperture of the one-piece body, to allow the septum hub to move from the first end of the aperture of the one-piece body to the second end of the aperture of the one-piece body.

22. The top connector of claim 17, wherein the top connector is lockable in a plurality of positions around a circumference to the septum hub.

23. A one-piece top connector configured for coupling with a medicine pump and a septum hub of an infusion set comprising:
    a. a one-piece body comprising:
       i. an aperture that passes through the one-piece body, wherein the aperture is configured to fit around of the septum hub; and
       ii. a septum pierce.

* * * * *